United States Patent
Benson

(10) Patent No.: US 7,923,614 B1
(45) Date of Patent: Apr. 12, 2011

(54) INBRED SUNFLOWER LINE CN1703

(75) Inventor: Robert Martin Benson, Ellsworth, WI (US)

(73) Assignee: Dow AgroSciences LLC, Indianapolis, IN (US)

( * ) Notice: Subject to any disclaimer, the term of this patent is extended or adjusted under 35 U.S.C. 154(b) by 1137 days.

(21) Appl. No.: 11/490,683

(22) Filed: Jul. 21, 2006

Related U.S. Application Data

(60) Provisional application No. 60/702,066, filed on Jul. 22, 2005.

(51) Int. Cl.
- *A01H 5/00* (2006.01)
- *A01H 5/10* (2006.01)
- *A01H 1/00* (2006.01)
- *A01H 4/00* (2006.01)
- *C12N 15/82* (2006.01)

(52) U.S. Cl. ........ 800/322; 800/260; 800/265; 800/266; 800/268; 800/269; 800/274; 435/410

(58) Field of Classification Search ................. 800/260, 800/265, 266, 268, 269, 274, 322; 435/410
See application file for complete search history.

(56) References Cited

U.S. PATENT DOCUMENTS
6,069,304 A * 5/2000 Cole .......................... 800/322

OTHER PUBLICATIONS
Dedio et al. 1980. Sunflower. In Fehr et al (ed.) Hybridization of crop plants, p. 631-644.*
Ozdemir et al. Plant Molecular Biol. Reporter 20: 239-249, 2002.*

* cited by examiner

*Primary Examiner* — Medina A. Ibrahim
*Assistant Examiner* — Keith O. Robinson
(74) *Attorney, Agent, or Firm* — Marcia I. Rosenfeld; Kenneth B. Ludwig

(57) ABSTRACT

An inbred sunflower line, designated CN1703, the plants and seeds of the inbred sunflower line CN1703, methods for producing a sunflower plant, either inbred or hybrid, produced by crossing the inbred sunflower line CN1703 with itself or with another sunflower plant, and hybrid sunflower seeds and plants produced by crossing the inbred line CN1703 with another sunflower line or plant and to methods for producing a sunflower plant containing in its genetic material one or more transgenes and to the transgenic sunflower plants produced by that method. This invention also relates to inbred sunflower lines derived from inbred sunflower line CN1703, to methods for producing other inbred sunflower lines derived from inbred sunflower line CN1703 and to the inbred sunflower lines derived by the use of those methods.

61 Claims, No Drawings

US 7,923,614 B1

INBRED SUNFLOWER LINE CN1703

FIELD OF THE INVENTION

This application claims the benefit of U.S. Provisional Application No. 60/702,066 filed on Jul. 22, 2005. This invention is in the field of sunflower breeding. In particular, the invention relates to an inbred sunflower line designated CN1703 that includes plants and seeds of inbred sunflower line CN1703. Methods for producing sunflower plants, such as inbred sunflower plants, hybrid sunflower plants, or other sunflower plants, as by crossing inbred sunflower line CN1703 with itself or any different sunflower plant are an integral part of this invention as are the resultant sunflower plants including the plant parts and seeds. This invention further relates to methods for producing CN1703-derived sunflower plants, to methods for producing male sterile CN1703 sunflower plants, e.g., cytoplasmic male sterile CN1703 sunflower plants and to methods for regenerating such plants from tissue cultures of regenerable cells as well as the plants obtained therefrom. Methods for producing a sunflower plant containing in its genetic material one or more transgenes and to the transgenic sunflower plants produced by that method are also a part of this invention.

BACKGROUND OF THE INVENTION

Sunflower (*Helianthus annuus* L.) now ranks second among all oilseed crops in the world as a source of edible vegetable oil. Sunflower is used as human food, livestock feed, and as raw material in industry. The food uses of sunflower include snack foods, cooking mediums and salad oils. Whole achenes are an important component of bird and other small animal feeds. Sunflower silage has utility as a livestock feed.

Sunflower oil is also used in the manufacture of margarine, soap, pharmaceuticals, shortening, lubricants and as a source for biodiesel fuels. Sunflower hulls can be pressed into logs for use in the fireplace and cooking stoves.

Sunflower hybrids can be classified into two broad categories: Confection (non-oil) and oil types. Confection sunflower seeds may be further divided into three classes: in-shell, kernel and birdseed. In-shell seed refers to larger sunflower seeds which may be roasted, salted and packaged for human consumption. Kernel seed refers to medium sized seeds which may be dehulled and also packaged for human consumption. Smaller seed may be sold in birdseed markets. Oil-type sunflower seed is richer in oil and therefore better suited to the production of sunflower oil and is used to produce ingredients for animal feed. Oil sunflower hybrids may be further divided into three classes: linoleic (regular oil type), NuSun (mid-oleic), and high oleic. A third category of sunflower seed referred to as hybrid seed has attributes of both confection and oil type sunflowers.

The goal of a sunflower breeder is to improve a sunflower plant's performance and therefore, its economic value by combining various desirable traits into a single plant. Improved performance is manifested in many ways. Higher yields of sunflower plants contribute to a more abundant food supply, a more profitable agriculture and a lower cost of food products for the consumer. Improved quality makes sunflower kernels more nutritious. Improved plant health increases the yield and quality of the plant and reduces the need for application of protective chemicals. Adapting sunflower plants to a wider range of production areas achieves improved yield and vegetative growth. Improved plant uniformity enhances the farmer's ability to mechanically harvest sunflower.

Sunflower is a dicot plant with perfect flowers, i.e., sunflower has male, pollen-producing organs and separate female, pollen receiving organs on the same flower. The cultivated sunflower inflorescence, or flower head is composed of about 700 to 3000 individual flowers attached to a common base called a receptacle. Ligulate ray flowers are present around the circumference of the receptacle but do not have stamens or pistils. The remaining flowers are disk flowers, which are arranged in arcs radiating from the center of the head. The disk flower is complete and consists of a basal inferior ovary, two pappus scales (modified sepals), a tubular corolla of five petals that are united, except for the tips, five anthers united to form a tube with separate filaments attached to the base of the corolla tube, and one style terminating in a divided stigma curled outward to the anther tube. Each floret matures over several days. At maturity each floret consists of separate male, longated pollen-shedding anther filaments and a female elongated pollen-receptive stigma.

Because sunflower has both male and female organs on the same flower, sunflower breeding techniques take advantage of the plant's ability to be bred by both self-pollination and cross-pollination. Self-pollination occurs when pollen from the male organ is transferred to a female organ on the same flower on the same plant. Self-incompatability is a form of infertility caused by the failure of sunflower plants with normal pollen and ovules to set seed due to some physiological hindrance that prevents fertilization. Self-incompatability restricts self-pollination and inbreeding and fosters cross-pollination. Cross-pollination occurs when pollen from the male organ on the flower of one plant is transferred to a female organ on the flower on a different plant.

A plant is sib-pollinated (a type of cross-pollination) when individuals within the same family or line are used for pollination (i.e. pollen from a family member plant is transferred to the stigmas of another family member plant). Self-pollination and sib-pollination techniques are traditional forms of inbreeding used to develop new inbred sunflower lines, but other techniques exist to accomplish inbreeding. New inbred sunflower lines are developed by inbreeding heterozygous plants and practicing selection for superior plants for several generations until substantially homozygous plants are obtained. During the inbreeding process with sunflower, the vigor of the lines decreases and after a sufficient amount of inbreeding, additional inbreeding merely serves to increase seed of the developed inbred. Inbred sunflower lines are typically developed for use in the production of hybrid sunflower lines.

Natural, or open pollination, occurs in sunflower when bees or other insects transfer pollen from the anthers to the elongated stigmas that protrude from the florets and may include both self- and cross-pollination. Such pollination is accomplished almost entirely by the bees or other pollinating insects and accordingly, interplant transfer of pollen by the wind is of little importance. Vigor is restored when two different inbred lines are cross-pollinated to produce the first generation ($F_1$) progeny. A cross between two defined homozygous inbred sunflower plants always produces a uniform population of heterozygous hybrid sunflower plants and such hybrid sunflower plants are capable of being generated indefinitely from the corresponding inbred sunflower seed supply.

When two different, unrelated inbred sunflower parent plants are crossed to produce an $F_1$ hybrid, one inbred parent is designated as the male, or pollen parent, and the other inbred parent is designated as the female, or seed parent. Because sunflower plants are capable of self-pollination, hybrid seed production requires elimination of or inactivation of pollen produced by the female parent to render the female parent plant male sterile. This serves to prevent the inbred sunflower plant designated as the female from self-pollinating. Different options exist for controlling male fertility in sunflower plants such as physical emasculation, genetic male sterility, cytoplasmic male sterility and application of gametocides. Incomplete removal of male parent plants from a hybrid seed production field before harvest provides the potential for unwanted production of self-pollinated or sib-pollinated seed which may be unintentionally harvested and packaged with hybrid seed.

The development of new inbred sunflower plants and hybrid sunflower plants is a slow, costly interrelated process that requires the expertise of breeders and many other specialists. The development of new hybrid sunflower varieties in a sunflower plant breeding program involves numerous steps, including: (1) selection of parent sunflower plants (germplasm) for initial breeding crosses; (2) inbreeding of the selected plants from the breeding crosses for several generations to produce a series of inbred lines, which individually breed true and are highly uniform; and, (3) crossing a selected inbred line with an unrelated line to produce the $F_1$ hybrid progeny having restored vigor.

Inbred sunflower plants and other sources of sunflower germplasm are the foundation material for all sunflower breeding programs. Despite the existence and availability of numerous inbred sunflower lines and other source germplasm, a continuing need still exists for the development of improved germplasm because existing inbred parent sunflower lines lose their commercial competitiveness over time. The present invention addresses this need by providing a novel inbred parent sunflower line designated CN1703 that contributes improved seed yield and oil yield per acre to hybrids relative to other similar hybrids in the same maturity groups. To protect and to enhance yield production, trait technologies and seed treatment options provide additional crop plan flexibility and cost effective control against insects, weeds and diseases, thereby further enhancing the potential of hybrids with CN1703 as a parent.

I. DEFINITIONS OF PLANT CHARACTERISTICS

In the description and examples that follow, a number of terms are used. To provide a clear and consistent understanding of the specification and claims, including the scope to be given such terms, the following definitions are provided.

Broom Rape: This represents a visual assessment of the sunflower plants for resistance to Broom Rape (*Orobanche cannis*) rated as 0=not tested, 1=susceptible, or 2=resistant.

Class: This represents the type of sunflower rated as 1=Oil Type, or 2=Non-oil type (confectionery).

Depth of Leaf Margin Indentations: This represents a visual assessment of the depth of margin indentations on a midstem at flowering rated as 1=shallow, 2=intermediate, or 3=deep.

Disk Flower Color: This represents a visual assessment of the color of the disk florets (corolla) at flowering rated as 1=yellow, 2=red, or 3=purple.

Downy Mildew: This represents a visual assessment of the sunflower plants for resistance to Downy Mildew (*Plasmorpara halstedii*) rated as 0=not tested, 1=susceptible, or 2=resistant.

Head Diameter: This represents the diameter (cm) of the head at seed maturity.

Inner Pericarp: This represents a visual assessment of the color of the inner pericarp (seed coat) rated as 1=no color or 2=brownish black.

Internode Length at Flowering: This represents the length (cm) of the midstem internode at flowering.

Leaf Apex: This represents the shape of a midstem leaf apex, i.e., the top portion of the leaf blade at flowering rated as 1=acuminate or 2=other.

Leaf Attitude: This represents the attitude of a midstem leaf at flowering rated as 1=erect, 2=ascending, 3=horizontal or 4=descending.

Leaf Base: This represents the shape of a midstem leaf base, i.e., the lower portion of the leaf blade where the petiole attaches at flowering rated as 1=auriculate, 2=truncate, 3=acute, 4=rounded, or 5=cordate.

Leaf Blade Length: This represents the length (cm) of a midstem leaf blade, i.e., the flat, expanded part of a leaf, from the leaf base to the leaf tip, exluding the petiole at flowering.

Leaf Blade Width: This represents the maximum width (cm) of a midstem leaf blade at flowering.

Leaf Color: This represents the color of a midstem leaf at flowering rated as 1=light green, 2=green, 3=dark green, or 4=brown.

Leaf Margin: This represents the appearance of a midstem leaf margin, i.e., the edge of a leaf at flowering rated as 1=entire, 2=crenate, or 3=serrate.

Leaf Margin Color: This represents the color of a midstem leaf margin at flowering represented as 1=green or 2=yellow.

Leaf Shape: This represents the shape of a midstem leaf at flowering rated as 1=cordate, 2=lanceolate, 3=triangular, or 4=round.

Leaf Surface: This represents the appearance of a midstem leaf at flowering rated as 1=smooth, 2=crinkled (ridged) or 3=other.

Leaf Width:Length Ratio: This represents a visual assessment of the width:length ratio of a midstem leaf at flowering rated as 1=narrower than long, 2=equal or 3=wider than long.

Middle Pericarp: This represents the color of the middle pericarp rated as 1=white or 2=solid purple.

No. of Days to Flowering: This represents the number of days from emergence to the R-5.1 stage of flowering of 50% of the plants.

No. of Days to Maturity: This represents the number of days from emergence to the R9 stage of maturity of 50% of the plants. This stage of development is regarded as physiological maturity and occurs when the back of a sunflower head is yellow and the bracts become yellow and brown.

No. of Seeds per Head: This represents the number of seeds per head at seed maturity.

Number of Leaves at Flowering: This represents the number of leaves on a plant at flowering.

Oil (%): This represents the amount of oil present expressed as a percentage for whole undecorticated seeds.

Oil Per Acre: This represents the oil yield in pounds per acre.

Oleic Acid (%): This represents the amount of oleic acid present expressed as a percentage of total oil for whole undecorticated seeds.

Outer Pericarp: This represents the color of the outer pericarp of the seed rated as 1=clear, 2=striped black, 3=nearly solid black.

Plant Height at Maturity: For inbreds, this represents this the average distance from the base of the stem to the base of the inflorescence in centimeters. For hybrids, this represents the average distance from the base of the stem to the base of the inflorescence in inches.

Pollen Color: This represents the color of the pollen at flowering represented as 1=white (colorless) or 2=yellow.

Ray Length: This represents the ray length (mm) on the head at flowering.

Ray Flowers: This represents the presence or absence of ray flowers on the head at flowering.

Ray Flower Color: This represents the color of the ray flowers, if present, on the head at flowering rated as 1=yellow, 2=sulfur yellow, 3=orange yellow or 4=other.

*Sclerotinia* Wilt: This represents a visual assessment of the sunflower plants for resistance to *Sclerotinia* Wilt (*Sclerotinia sclerotiorum*) rated as 0=not tested, 1=susceptible, or 2=resistant.

Seed Length: For inbreds, this represents the average length (mm) of whole, undecorticated seed. For hybrids, this represents the average length (cm) of whole, undecorticated seed.

Seed Moisture: This represents the percent seed moisture at harvest.

Seed Mottling: This represents spots or blotches of color on the outer surface of the hull as measured by visual assessment of a group of seeds rated as 1=absent or 2=present.

Seed Shape: This represents the overall shape of undecorticated seed rated as 1=ovate, 2=obovate (shield), 3=narrowly obovate, 4=oblong or 5=elliptic.

Seed Shape (Cross Section): This represents the cross-sectional shape of undecorticated seed rated as 1=not curved or 2=curved.

Seed Size (% Held on 7.9 mm (20/64) Round-hole Screen): This represents the percentage of undecorticated seed held on a 7.9 mm (20/64) Round-hole screen.

Seed Stripes: This represents the coloration, if any, present on the outer pericarp rated as 1=absent, 2=even black and white stripes, 3=broad black and narrow white stripes, 4=black with narrow dark-grey striping or 5=other.

Seed Weight: This represents the weight (gm) of 100 undecorticated seeds.

Stem Branching: This represents the branching habit at flowering rated as 1=No Branching, 2=Basal Branching, 3=Top Branching (with central head), and 4=Fully Branched (without central head).

Stem Color of Growing Point: This represents the stem color of the growing point during active growth and development rated as 1=Green or 2=Yellow.

T Distribution Probability: This represents the T distribution probability.

Test Weight Per Bushel: This represents the number of pounds of hybrid seed per bushel volume.

Yield: This represents the seed yield in pounds per acre adjusted to 10% moisture.

Yield Performance: This represents the percent performance of a hybrid relative to a check hybrid in a side-by-side comparison for grain yield in pounds per acre over multiple years and locations.

II. INBRED SUNFLOWER LINE CN1703

A. Inbred Sunflower Plant CN1703

In accordance with one aspect of the present invention, provided is a new inbred sunflower seed and plants thereof designated CN1703. This inbred may optionally further carry the designation "A" or "B" where the "A" designation indicates that this inbred sunflower seed and plants thereof have sterile cytoplasm and recessive, nonrestorer genes and where the "B" designation indicates that this inbred sunflower seed and plants thereof have normal instead of sterile cytoplasm, and recessive, nonrestorer genes. The present invention further relates to a method for producing inbred sunflower seeds that includes, but is not limited to, the steps of planting seed of inbred sunflower CN1703 in proximity to itself, or to different seed from a same family or line, growing the resulting sunflower plants under self-pollinating or sib-pollinating conditions with adequate isolation, and harvesting resultant seed obtained from such inbred plants using techniques standard in the agricultural arts such as would be necessary to produce more B-line (maintainer) seed or to bulk-up A-line seed such as for hybrid production. The present invention also relates to inbred seed produced by such a method.

In any cross between inbred sunflower plant CN1703 and another, different inbred sunflower plant, CN1703 may be designated as the male (pollen parent) or the female (seed producing parent). In a particular embodiment CN1703 is designated as the female parent. Optionally, the seed of inbred sunflower line CN1703 may be pre-treated to increase resistance of the seed and/or seedlings to stressed conditions, and further, the sunflower plants or surrounding soil may be treated with one or more agricultural chemicals before harvest. Such agricultural chemicals may include herbicides, insecticides, pesticides and the like. The present invention also relates to sunflower plant that expresses substantially all of the physiological and morphological characteristics of inbred sunflower plant CN1703 and to a substantially homogenous population of sunflower plants having all the physiological and morphological characteristics of inbred sunflower plant CN1703. Any sunflower plants produced from inbred sunflower plant CN1703 are contemplated by the present invention and are, therefore, within the scope of this invention. A description of physiological and morphological characteristics of sunflower plant CN1703B is presented in Table 1.

TABLE 1

| Characteristic | Value |
| --- | --- |
| CLASS (1 = Oil Type, or 2 = Confectionery, non-oil type) | 1 |
| NO. OF DAYS TO FLOWERING | 80 |
| NO. OF DAYS TO MATURITY | 119 |
| PLANT HEIGHT AT MATURITY (cm) | 112 |
| NUMBER OF LEAVES AT FLOWERING | 29 |
| STEM BRANCHING 1 = No Branching, 2 = Basal Branching, 3 = Top Branching (with central head), and 4 = Fully Branched (without central head). | 1 |
| INTERNODE LENGTH AT FLOWERING (cm) | 6.3 |
| STEM COLOR OF GROWING POINT (1 = Green or 2 = Yellow) | 1 |
| DEPTH OF LEAF MARGIN INDENTATIONS (1 = shallow, 2 = intermediate, or 3 = deep) | 2 |

TABLE 1-continued

| Characteristic | Value |
|---|---|
| LEAF APEX (1 = acuminate or 2 = other) | 1 |
| LEAF ATTITUDE (1 = erect, 2 = ascending, 3 = horizontal or 4 = descending) | 2 |
| LEAF BASE 1 = auriculate, 2 = truncate, 3 = acute, 4 = rounded, or 5 = cordate | 1 |
| LEAF BLADE LENGTH (cm) | 20.5 |
| LEAF BLADE WIDTH (cm) | 22.5 |
| LEAF COLOR (1 = light green, 2 = green, 3 = dark green, or 4 = brown) | 2 |
| LEAF MARGIN (1 = entire, 2 = crenate, or 3 = serrate) | 2 |
| LEAF MARGIN COLOR (1 = green or 2 = yellow) | 1 |
| LEAF SHAPE (1 = cordate, 2 = lanceolate, 3 = triangular, or 4 = round) | 1 |
| LEAF SURFACE (1 = smooth, 2 = crinkled (ridged) or 3 = other) | 2 |
| LEAF WIDTH:LENGTH RATIO (1 = narrower than long, 2 = equal or 3 = wider than long) | 3 |
| RAY FLOWERS (presence or absence) | Present |
| RAY FLOWER COLOR (1 = yellow, 2 = sulfur yellow, 3 = orange yellow or 4 = other) | 1 |
| DISK FLOWER COLOR (1 = yellow, 2 = red, or 3 = purple) | 1 |
| POLLEN COLOR (1 = white (colorless) or 2 = yellow) | 2 |
| HEAD DIAMETER (cm) | 20.3 |
| NO. OF SEEDS PER HEAD | 710 |
| OUTER PERICARP (1 = clear, 2 = striped black, 3 = nearly solid black) | 3 |
| MIDDLE PERICARP (1 = white or 2 = solid purple) | 1 |
| INNER PERICARP (1 = no color or 2 = brownish black) | 1 |
| SEED LENGTH (mm) | 9.5 |
| SEED MOTTLING (1 = absent or 2 = present) | 1 |
| SEED SHAPE (1 = ovate, 2 = obovate (shield), 3 = narrowly obovate, 4 = oblong or 5 = elliptic) | 2 |
| SEED SHAPE (CROSS SECTION) (1 = not curved or 2 = curved) | 2 |
| SEED SIZE (% Held on 7.9 mm (20/64) Round-hole Screen) | 0 |
| SEED STRIPES (1 = absent, 2 = even black and white stripes, 3 = broad black and narrow white stripes, 4 = black with narrow dark-grey striping or 5 = other) | 4 |
| SEED WEIGHT (gm) | 68.4 g/1000 sds |
| BROOM RAPE (1 = susceptible, or 2 = resistant) | 1 |
| DOWNY MILDEW (1 = susceptible, or 2 = resistant) | 1 |
| SCLEROTINIA WILT (1 = susceptible, or 2 = resistant) | 1 |
| OIL (%) | 40.2 |

It should be appreciated by one having ordinary skill in the art that, for the quantitative characteristics identified in Table 1, the values presented are typical values. These values may vary due to the environment and accordingly, other values that are substantially equivalent are also within the scope of the invention.

Inbred sunflower line CN1703B shows uniformity and stability within the limits of environmental influence for the traits described in Table 1. Inbred CN1703 has been self-pollinated and head-rowed a sufficient number of generations with careful attention paid to uniformity of plant type to ensure the homozygosity and phenotypic stability necessary to use in large scale, commercial production. The line has been increased both by hand and sib-pollinated in isolated fields with continued observations for uniformity. No variant traits have been observed or are expected in CN1703.

The present invention also relates to one or more sunflower plant parts of inbred sunflower plant CN1703. Sunflower plant parts include an intact plant cell, a plant protoplast, an embryo, an ovule, a pollen, a stigma, a flower head, a seed, a hull, a leaf, a root, a root tip, an anther, a cortex, a pith, an involucral bract, a ray flower, a disk flower, a pappi, a stalk, a nectary, an interfloral bact, a trichome, a filament, a calyx and a stem and the like.

B. Inbred Sunflower Seed Designated CN1703

A sunflower kernel is composed of four structural parts: (1) the pericarp, which is a protective outer covering (also known as bran or hull) which comprises an inner pericarp (seed coat), middle pericarp, and outer pericarp; (2) the germ (also known as an embryo); (3) the endosperm; and, (4) the tip cap, which is the point of attachment to the receptacle. Another aspect of the present invention is one or more parts of inbred sunflower seed CN1703, such as the pericarp of inbred sunflower seed CN1703 or the germ and/or the endosperm of inbred sunflower seed CN1703 which remain upon removal of the pericarp and adhering remnants of the seed coat.

Inbred sunflower seed designated CN1703 may be provided as a substantially homogenous composition of inbred sunflower seed designated CN1703, that is, a composition that consists essentially of inbred sunflower seed CN1703. Such a substantially homogenous composition of inbred sunflower seed CN1703 is substantially free from significant numbers of other inbred and/or hybrid seed so that the inbred seed forms from about 90% to about 100% of the total seed. Preferably, a substantially homogenous composition of the inbred sunflower seed contains from about 98.5%, 99%, or 99.5% to about 100% of the inbred seed, as measured by seed grow outs. The substantially homogenous composition of inbred sunflower seed of the invention may be separately grown to provide substantially homogenous populations of inbred sunflower plants. However, even if a population of inbred sunflower plants is present in a field with other different sunflower plants, such as in a commercial seed-production field of single-cross hybrid sunflower planted in a ratio of 1 male pollinator row to 3 female seed-parent rows, such a population would still be considered to be within the scope of the present invention.

Sunflower yield is affected by the conditions to which seeds and seedlings (young plants grown from seeds) are exposed. Seeds and seedlings may be exposed to one of, or a combination of, for example, cold, drought, salt, heat, pollutants, and disease, all of which are conditions that potentially retard or prevent the growth of crops therefrom. Furthermore, diseases evolved from pathogens and deterioration caused by fungi are potentially harmful to seeds and seedlings. Thus, it is desirable to treat seeds as by coating or impregnating the seeds with compositions that render the seeds and seedlings grown therefrom more hardy when exposed to such adverse conditions.

Accordingly, another aspect of the present invention relates to a coated and/or impregnated seed or sunflower inbred line designated CN1703, CN1703B, and CN1703A and to coated and/or impregnated seed derived therefrom. Various agents have been used to treat seeds to increase resistance of the plants to stressed conditions, such as cold, drought, salt, and fungi. Such agents include, for example, sodium methylphenyl-pentadienate, trichloroacetic acid, polyoxyalkylene-organo-siloxane block copolymer, 5-aminolevulinic acid, salicylic acid, thiamethoxam, potassium chloride, and polyvinyl alcohol and are useful alone, or in combination in the present invention.

When pre-treating seeds according to the present invention such as before the seeds are planted, the seeds are contacted with the composition of interest, as by coating seeds, spraying seeds, and soaking seeds or a combination thereof, by methods well known to those skilled in the art.

C. Deposit Information

Applicants have made a deposit of at least 2,500 seeds of inbred sunflower plant CN1703 with the American Type Culture Collection (ATCC), Manassas, Va. 20110 USA, under ATCC Accession No. PTA-6885. The seeds deposited with the ATCC on Jun. 22, 2005 were taken from a deposit maintained by Agrigenetics, Inc. d/b/a Mycogen Seeds since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will maintain and will make this deposit available to the public pursuant to the Budapest Treaty.

A. Novel Inbred Sunflower Plants Obtained From Inbred CN1703

Various breeding schemes may be used to produce new inbred sunflower lines from CN1703. In one method, generally referred to as the pedigree method, CN1703 may be crossed with another different sunflower plant such as a second inbred parent sunflower plant, which either itself exhibits one or more selected desirable characteristic(s) or imparts selected desirable characteristic(s) to a hybrid combination. Examples of potentially desired characteristics include greater yield, better stalks, better roots, reduced time to crop maturity, better agronomic quality, higher nutritional value, improved oil quality, improved oil quantity, resistance and/or tolerance to insecticides, herbicides, pests, heat and drought, and disease, and uniformity in germination times, stand establishment, growth rate, maturity and kernel size. If the two original parents sunflower plants do not provide all the desired characteristics, then other sources can be included in the breeding population. Elite inbred lines, that is, pure breeding, homozygous inbred lines, can also be used as starting materials for breeding or source populations from which to develop inbred lines.

Thereafter, resulting seed is harvested and resulting superior progeny plants are selected and selfed or sib-mated in succeeding generations, such as for about 5 to about 7 or more generations, until a generation is produced that no longer segregates for substantially all factors for which the inbred parents differ, thereby providing a large number of distinct, pure-breeding inbred lines.

In another embodiment for generating new inbred sunflower plants, generally referred to as backcrossing, one or more desired traits may be introduced into inbred parent sunflower plant CN1703 (the recurrent parent) by crossing the CN1703 plants with another sunflower plant (referred to as the donor or non-recurrent parent) which carries the gene (s) encoding the particular trait(s) of interest to produce $F_1$ progeny plants. An exemplary donor or non-recurrent parent is any source of cytoplasmic male sterility. Both dominant and recessive alleles may be transferred by backcrossing. The donor plant may also be an inbred, but in the broadest sense can be a member of any plant variety or population cross-fertile with the recurrent parent. Next, $F_1$ progeny plants that have the desired trait are selected. Then, the selected progeny plants are crossed with CN1703 to produce backcross progeny plants. Thereafter, backcross progeny plants comprising the desired trait and the physiological and morphological characteristics of sunflower inbred line CN1703 are selected. This cycle is repeated for about one to about eight cycles, preferably for about 3 or more times in succession to produce selected higher backcross progeny plants that comprise the desired trait and all of the physiological and morphological characteristics of sunflower inbred line CN1703B listed in Table 1 as determined at the 5% significance level when grown in the same environmental conditions. Exemplary desired trait(s) include insect resistance, cytoplasmic male sterility, enhanced nutritional quality, herbicide resistance, yield stability, yield enhancement and resistance to bacterial, fungal and viral disease. High oil percentage and fatty acid composition are important in breeding oilseed types whereas large seed size, a high kernel-to-hull ratio, and uniformity in seed size, shape, and color are important objectives in breeding and selection of non-oilseed sunflower. One of ordinary skill in the art of plant breeding would appreciate that a breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walter, Principles of Cultivar Development, Vol. 1, p. 261-286 (1987) which is incorporated herein by reference. Mean trait values may be used to determine whether trait differences are significant, and preferably the traits are measured on plants grown under the same environmental conditions.

This method results in the generation of inbred sunflower plants with substantially all of the desired morphological and physiological characteristics of the recurrent parent and the particular transferred trait(s) of interest. Because such inbred sunflower plants are heterozygous for loci controlling the transferred trait(s) of interest, the last backcross generation would subsequently be selfed to provide pure breeding progeny for the transferred trait(s).

Backcrossing may be accelerated by the use of genetic markers such as SSR, RFLP, SNP or AFLP markers to identify plants with the greatest genetic complement from the recurrent parent.

Direct selection may be applied where a single locus acts as a dominant trait, such as the herbicide resistance trait. For this selection process, the progeny of the initial cross are sprayed with the herbicide before the backcrossing. The spraying eliminates any plants which do not have the desired herbicide resistance characteristic, and only those plants which have the herbicide resistance gene are used in the subsequent backcross. In the instance where the characteristic being transferred is a recessive allele, it may be necessary to introduce a test of the progeny to determine if the desired characteristic has been successfully transferred. The process of selection, whether direct or indirect, is then repeated for all additional backcross generations.

It should be appreciated by those having ordinary skill in the art that backcrossing can be combined with pedigree breeding as where inbred CN1703 is crossed with another sunflower plant, the resultant progeny are crossed back to inbred CN1703B and thereafter, the resulting progeny of this single backcross are subsequently inbred to develop new inbred lines. This combination of backcrossing and pedigree breeding is useful as when recovery of fewer than all of the CN1703 characteristics than would be obtained by a conventional backcross are desired.

In an additional embodiment of the present invention, new inbred sunflower plants can be developed by a method generally referred to as haploid breeding. In this methodology, haploid plants are generated from diploid, heterozygous sunflower plants that result from crossing inbred sunflower plant CN1703 with another, different sunflower plant. Such haploid sunflower plants may be generated by methods known to those skilled in the art such as by culturing haploid anthers or embryos from a diploid plant. Alternately, such haploid sunflower plant may be generated by crossing the diploid heterozygous sunflower plant with a sunflower plant that comprises a haploid inducing gene, which, when present in the female parent results in offspring with a greatly enhanced frequency of haploids of both maternal and paternal origin. Thereafter, homozygous diploid plants are produced by the doubling of a set of chromosomes (1N) from a haploid plant generated by self-pollination such as through use of a doubling agent, such as colchicine, nitrous oxide gas, heat treatment and trifluralin. See, e.g., Todorova et al., "Doubled haploid production of sunflower (*Helianthus annuus* L.) through irradiated pollen-induced parthenogenesis", Euphytica, Vol. 97, Number 3: 249-254, January 1997, the disclosure of which is expressly incorporated herein by reference. The technique of haploid breeding is advantageous because no subsequent inbreeding is required to obtain a homozygous plant from a heterozygous source. Thus, in another aspect of this invention a new inbred sunflower plant is developed by a method that includes the steps of crossing CN1703 or a hybrid made with CN1703 with another inbred sunflower plant having a propensity to generate haploids to produce haploid progeny plants, and selecting desirable inbred sunflower plants from the haploid progeny plants.

The present invention also relates to novel sunflower plants produced by a method generally referred to as mutation breeding whereby one or more new traits may be artificially introduced into inbred line CN1703. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis and selected, the trait may then be incorporated into existing germplasm by traditional breeding techniques. Details of mutation breeding can be found in "Principals of Cultivar Development" Fehr, 1993 Macmillan Publishing Company the disclosure of which is incorporated herein by reference.

The mutagenesis treatment may be applied to various stages of plant development, including but not limited to cell cultures, embryos, microspores and shoot apices as well as to sunflower kernels. By way of example, pollen may be mixed with a solution of 1 ml EMS and 100 mls Fisher paraffin oil (stock diluted by 1 ml and 15 mls oil solution) every minute for the first 5 minutes and then every five minutes for 45 minutes to keep the pollen suspended. Thereafter, the pollen/paraffin oil solution is brushed onto the stigmas of developing florets. A cover may be used to prevent the stigmas from contamination. The head is picked at maturity and then resultant seeds or the plants therefrom are screened for the desired mutant trait(s).

Once inbred lines are created, the next step is to determine if the inbreds have any value. This is accomplished by techniques of measuring the combining ability of the new inbred plant, as well as the performance of the line itself. Combining ability refers to a line's contribution as a parent when crossed with other lines to form hybrids. Specific combining ability (SCA) refers to the ability of a line to cross to another specific inbred to form a hybrid. General combining ability (GCA) refers to the ability of a line to cross to a wide range of lines to form hybrids. The methodology of forming hybrids to evaluate an inbred line's contribution as a parent for the purpose of selecting superior lines is interchangeably known as experimental, top or test crossing.

B. Novel Inbred Sunflower Plants Obtained from a Hybrid Having Inbred CN1703 as a Parent In accordance with processes of the present invention, a hybrid sunflower plant having inbred CN1703 as a parent, e.g., CN1703A is crossed with itself or any different sunflower plant such as an inbred sunflower plant or a hybrid sunflower plant to develop a novel inbred line. For example, a hybrid sunflower plant having inbred sunflower plant CN1703 as a parent may be inbred, i.e., crossed to itself or sib-pollinated, and the resulting progeny each selfed for about 5 to about 7 or more generations, thereby providing a set of distinct, pure-breeding inbred lines wherein each of the lines received all of its alleles from the hybrid sunflower plant having inbred sunflower plant CN1703 as a parent. Double haploid methods can also be used to obtain an inbred sunflower plant that is homozygous at essentially every locus, wherein the inbred sunflower plant received all of its alleles from the hybrid sunflower plant having inbred sunflower plant CN1703 as a parent. In other embodiments, a hybrid sunflower plant having inbred sunflower plant CN1703 as a parent is crossed with a different sunflower plant that is recessive nonrestorer. Different sunflower plants may include any inbred sunflower plant that is not inbred sunflower plant CN1703, any hybrid sunflower plant that does not have CN1703 as a parent, another germplasm source, a haploid or mutation inducing stock, or a trait donor plant, thereby providing a set of distinct, pure-breeding inbred lines. The resulting inbred lines could then be crossed with other inbred or non-inbred lines and the resulting inbred progeny analyzed for beneficial characteristics. In this way, novel inbred lines conferring desirable characteristics could be identified.

C. "Chasing Selfs"

Male inbred seed may occasionally be found within a commercial bag of sunflower hybrid seed. Chasing the selfs involves identifying inbred plants within a stand of sunflower that has been grown from a bag of hybrid sunflower seed. Once the seed is planted, the inbred plants may be identified and selected due to their decreased vigor, i.e., by their short stature, narrower leaves, and smaller heads relative to the hybrid plants that grow from the hybrid seed which predominates in a commercial bag of hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another embodiment of the present invention is directed to a method for producing inbred sunflower plant CN1703, comprising: (a) planting a collection of seed, such as a collection of seed comprising seed of a hybrid, one of whose parents is inbred sunflower plant CN1703, the collection also comprising seed of the inbred; (b) growing plants from said collection of seed; (c) identifying inbred parent plants; (d) controlling pollination in a manner which preserves homozygosity of the inbred parent plant; and, (e) harvesting resultant seed. Step (c) may further comprise identifying plants with decreased vigor, i.e., plants that appear less robust than the other plants, or identifying plants that have a genetic profile in accordance with the genetic profile of CN1703, such as an SSR genetic profile in accordance with Table 3 herein. Sunflower plants capable of expressing substantially all of the physiological and morphological characteristics of inbred sunflower plant CN1703 include sunflower plants obtained by chasing selfs from a bag of hybrid seed.

One having skill in the art will recognize that once a breeder has obtained inbred sunflower plant CN1703 by chasing selfs from a bag of hybrid seed, the breeder can then produce new inbred plants such as by self-pollinating or sib-pollinating, i.e., crossing the inbred sunflower plant CN1703 with another inbred sunflower plant CN1703, or by crossing the inbred sunflower plant CN1703 with a hybrid sunflower plant obtained by growing the collection of seed.

IV. NOVEL HYBRID PLANTS

A. Novel Hybrid Seeds and Plants

In yet another aspect of the invention, processes are provided for producing sunflower seeds or plants, which processes generally comprise crossing a first parent sunflower plant with a second parent sunflower plant wherein at least one of the first parent sunflower plant or the second parent sunflower plant is inbred parent sunflower plant CN1703. These processes may be further exemplified as processes for preparing hybrid sunflower seed or plants, wherein a first inbred sunflower plant is crossed with a second sunflower plant of a different, distinct variety to provide a hybrid that has, as one of its parents, the inbred sunflower plant variety CN1703. In this case, a second inbred variety is selected which confers desirable characteristics when in hybrid combination with the first inbred line. In these processes, crossing will result in the production of seed. The seed production occurs regardless whether the seed is collected.

Any time the inbred sunflower plant CN1703 is crossed with another, different sunflower inbred, a first generation ($F_1$) sunflower hybrid plant is produced. As such, an $F_1$ hybrid sunflower plant may be produced by crossing CN1703 with any second inbred sunflower plant. Therefore, any $F_1$ hybrid sunflower plant or sunflower seed which is produced with CN1703 as a parent is part of the present invention.

When inbred sunflower plant CN1703 is crossed with another inbred plant to yield a hybrid, the original inbreds can serve as either the maternal or paternal plant with basically, the same characteristics in the hybrids. Occasionally, maternally inherited characteristics may express differently depending on the decision of which parent to use as the female. However, often one of the parental plants is preferred as the maternal plant because it has sterile cytoplasm or because of increased seed yield and preferred production characteristics, such as optimal seed size and quality or ease of head removal. Seed coat characteristics can be preferable in one plant which may affect shelf life of the hybrid seed product. Pollen can shed better by one plant, thus rendering that plant as the preferred male parent. For example, preferred male parent plants may have a recessive gene for branching. Such plants will produce multiple heads, thereby extending the pollen shed period of a plant. In some embodiments, CN1703 is used as a female parent, i.e., it is male-sterile and carries the "A" designation.

In embodiments of the present invention, the first step of "crossing" the first and the second parent sunflower plants comprises planting, preferably in pollinating proximity, seeds of a first inbred sunflower plant and a second, distinct inbred sunflower plant. As discussed herein, the seeds of the first inbred sunflower plant and/or the second inbred sunflower plant can be treated with compositions that render the seeds and seedlings grown therefrom more hardy when exposed to adverse conditions. Generally, one parent plant has sterile cytoplasm and recessive, nonrestorer genes and the other parent, known as the R-line, hay have either normal or sterile cytoplasm and dominant, fertility-restorer genes conferring male fertility in sunflower plants having the sterile cytoplasm.

A further step comprises cultivating or growing the seeds of the first and second parent sunflower plants into plants that bear flowers. If the parental plants differ in timing of sexual maturity, techniques may be employed to obtain an appropriate nick, i.e., to ensure the availability of pollen from the parent sunflower plant designated the male during the time at which stigmas on the parent sunflower plant designated the female are receptive to the pollen. Methods that may be employed to obtain the desired nick include delaying the flowering of the faster maturing plant, such as, but not limited to delaying the planting of the faster maturing seed or planting the seed of the faster maturing plant at a greater depth.

In a preferred embodiment, the sunflower plants are treated with one or more agricultural chemicals as considered appropriate by the grower.

A subsequent step comprises preventing self-pollination or sib-pollination of the plants, i.e., preventing the stigmas of a plant from being fertilized by any plant of the same variety, including the same plant. This is preferably done in large scale production by controlling the male fertility, e.g., treating the flowers so as to prevent pollen production or alternatively, using as the female parent a male sterile plant of the first or second parent sunflower plant (i.e., treating or manipulating the flowers so as to prevent pollen production, to produce an emasculated parent sunflower plant or using as a female, a cytoplasmic male sterile version of the sunflower plant). In large scale production, the male plants may be physical removed immediately after pollination.

Yet another step comprises allowing cross-pollination to occur between the first and second parent sunflower plants. If the male parent plant is located adjacent to the female parent plant and is shedding pollen, the receptacles can be rubbed together to consummate the transfer of pollen. When the plants are not in pollinating proximity and if the flower of the male parent can be sacrificed, the male head can be removed from the stem and carried to the female plant for pollination. Alternately, the pollen can be transferred by rubbing pollen onto the stigmas from the cloth or leaf used for collection. A cotton swab or a small paintbrush can be used to transfer pollen from a paper bag or glass container onto the stigmas. In large scale production, crossing is accomplished by isolated open-pollinated crossing fields whereby sunflower plants of the parent designated as the female, which are controlled for male fertility, are allowed to be pollinated by other plants of a different sunflower type where such plants are adjacent to the plants designated as the female parent. In embodiments of the present invention, an external source of pollinating insects, e.g. bees may be placed in the area of isolation to facilitate pollination.

A distinct advantage of sunflower over the majority of other crop species is that pollen can be collected and stored for several weeks utilizing proper refrigeration and humidity. Pollen in paper bags can be viable after 4 weeks of storage in a refrigerator at a temperature of 6° C. Pollen that has been desiccated and stored in sealed bottles has remained viable up to 1 year. Pollen should be stored free of other plant materials or insects and placed in a cold container after collection in the field.

A further step comprises harvesting the seeds, near or at maturity, from the plant that received the pollen. In a particular embodiment, seed is harvested from the female parent plant, and when desired, the harvested seed can be grown to produce a first generation ($F_1$) hybrid sunflower plant.

Yet another step comprises drying and conditioning the seeds, including the treating, sizing (or grading) of seeds, and packaging for sale to growers for the production of grain or forage. As with inbred seed, it may be desirable to treat hybrid seeds with compositions that render the seeds and seedlings grown therefrom more hardy when exposed to adverse conditions. Mention should be made that resulting hybrid seed is sold to growers for the production of grain and forage and not for breeding or seed production.

Still further, the present invention provides a hybrid sunflower plant produced by growing the harvested seeds produced on the male-sterile plant as well as grain produced by the hybrid sunflower plant.

A single cross hybrid is produced when two different inbred parent sunflower plants are crossed to produce first generation $F_1$ hybrid progeny. Generally, each inbred parent sunflower plant has a genotype which complements the genotype of the other inbred parent. A single cross hybrid may be produced by crossing a male sterile female (i.e., an A-line) with a male fertile restorer line (i.e., an R-line). Typically, the $F_1$ progeny are more vigorous then the respective inbred parent sunflower plants. This hybrid vigor, or heterosis, is manifested in many polygenic traits, including markedly improved yields and improved stalks, roots, uniformity and insect and disease resistance. It is for this reason that single cross $F_1$ hybrids are generally the most sought after hybrid. A three-way hybrid is produced from three inbred lines (or synthetics) where two of the inbred lines are crossed (A×B) and then the resulting $F_1$ hybrid is crossed with the third inbred (A×B)×C, as where a modified female is used in the cross. A modified female provides an advantage of improved seed parent yield whereas a modified male improves pollen flow. By way of example, a three way hybrid may be made by crossing an A-line with an unrelated maintainer line (B-line) to produce a male sterile single cross hybrid. This hybrid is crossed with an R-line to produce a male-fertile three-way hybrid. An advantage for using three-way hybrids is the lower cost of producing hybrid seed compared with single cross hybrids.

A modified single cross hybrid, also referred to as a modified three-way hybrid is produced by crossing an A-line with a genetically related B-line, an crossing the resulting male-sterile hybrid with an R-line. Three-way hybrids can be quite heterogenous in many characteristics depending on the differences in height, days to flowering, and other traits among the three parents, which is a disadvantage for production regions where uniformity is desirable. Modified single-cross hybrids are more uniform than three-way hybrids and less expensive to produce than single-cross hybrids. Single-cross hybrids are the most uniform type of hybrid and generally have the highest yield in commercial production A double cross hybrid is produced from four inbred lines crossed in pairs (A×B and C×D), thereby resulting in two $F_1$ hybrids that are crossed again. Double cross hybrids are more common in countries wherein less demand exists for higher yielding single cross hybrids. Synthetic populations or crosses are developed by crossing two or more inbred lines (or hybrids, or germplasm sources) together and then employing one of many possible techniques to random mate the progeny. Random mating the progeny is any process used by plant breeders to make a series of crosses that will create a new germplasm pool from which new breeding lines can be derived. Much of the hybrid vigor exhibited by $F_1$ hybrids is lost in the next generation ($F_2$). Consequently, seed from hybrids are not typically used for planting stock.

The utility of the inbred sunflower plant CN1703 also extents to crosses with species other than the *annus* species, such as *petiolaris* Nutt., *maximiliani* Schrader, *tuberosus*, and *giganteus* L. Commonly, suitable species will be of the tribe Heliantheae and of the family Asteraceae.

B. Physical Description of $F_1$ Hybrids and $F_1$ Hybrid Comparison

As mentioned above, testcross hybrids are progressively eliminated following detailed evaluations of their phenotype, including formal comparisons with other commercially successful hybrids. Research small-plot trials and commercial strip trials are used to compare the phenotypes of hybrids grown in as many environments as possible. They are performed in many environments to assess overall performance of the new hybrids and to select optimum growing conditions. Because the sunflower is grown in close proximity, differential effects of environmental factors that affect gene expression, such as moisture, temperature, sunlight, and pests, are minimized. For a decision to be made to advance a hybrid, it is not necessary that the hybrid be better than all other hybrids. Rather, significant improvements must be shown in at least some traits that would create value for some applications or markets. Some testcross hybrids are eliminated despite being similarly competitive relative to the current commercial hybrids because of the cost to bring a new hybrid to market requires a new product to be a significant improvement over the existing product offering. Such hybrids may also be licensed to other parties who have a need in their commercial product portfolio.

The present invention provides F1 hybrid sunflower plants obtained from the sunflower plant CN1703. The physical characteristics of exemplary hybrids produced using CN1703 as one inbred parent are set forth in Table 2. The results in Table 2 present a comparison of performance data for a hybrid made with CN1703A as one parent, versus DAS 8N421.

TABLE 2

| Characteristic | 8N510 (CN1703A × H1063R) | 8N421 (CN1701A × H1063R) | Experiments | Environments | Years |
|---|---|---|---|---|---|
| No. of Days to | 72 | 70 | 8 | 8 | 4 |
| Plant Height at Maturity (in) | 68 | 72 | 9 | 9 | 4 |
| Test Weight Per Bushel (lb/bu) | 26.5 | 27.3 | 13 | 13 | 4 |
| Seed Moisture | 10.9 | 10.4 | 21 | 21 | 4 |
| Yield | 2417 | 2268 | 21 | 21 | 4 |
| Yield Performance (% of Hybrid B) | 107 | | | | |
| Oil (%) | 41.6 | 44.2 | 12 | 12 | 4 |
| Oil Per Acre (lb/ac) | 1005 | 1003 | 21 | 21 | 4 |
| Oleic (%) | 62.9 | 63.8 | 6 | 6 | 4 |

V. NOVEL CN1703A/B-DERIVED PLANTS

All plants produced using inbred sunflower plant CN1703 as a parent are within the scope of this invention, including plants derived from inbred sunflower plant CN1703. This includes plants essentially derived from inbred CN1703 with the term "essentially derived variety" having the meaning ascribed to such term in 7 U.S.C. §2104(a)(3) of the Plant Variety Protection Act, which definition is hereby incorporated by reference. This also includes progeny plant and parts thereof with at least one ancestor that is inbred sunflower plant CN1703 and more specifically where the pedigree of this progeny includes 1, 2, 3, 4, 5 and/or more such as 6, 7, 8, 9 and/or 10 cross pollinations to inbred sunflower plant CN1703, or a plant that has CN1703 as a progenitor. All breeders of ordinary skill in the art maintain pedigree records of their breeding programs. These pedigree records contain a detailed description of the breeding process, including a listing of all parental lines used in the breeding process and information on how such line was used. Thus, a breeder would know if CN1703 were used in the development of a progeny line, and would also know how many breeding crosses to a line other than CN1703 were made in the development of any progeny line. A progeny line so developed may then be used in crosses with other, different, sunflower inbreds to produce first generation F1 sunflower hybrid seeds and plants with superior characteristics.

Accordingly, another aspect of the present invention is methods for producing an inbred sunflower line CN1703-derived sunflower plant. This method for producing a CN1703-derived sunflower plant, comprises: (a) crossing inbred sunflower plant CN1703 with a second sunflower plant to yield progeny sunflower seed; and, (b) growing the progeny sunflower seed, (under plant growth conditions), to yield the CN1703-derived sunflower plant. Such methods may further comprise the steps of: (c) crossing the CN1703-derived sunflower plant with itself or another sunflower plant to yield additional CN1703-derived progeny sunflower seed; (d) growing the progeny sunflower seed of step (b) (under plant growing conditions), to yield additional CN1703-derived sunflower plants; and (e) repeating the crossing and growing steps of (c) and (d) from 0 to 7 times or more such as even 8, 9 or 10 times to generate further CN1703-derived sunflower plants. Still further, this may comprise utilizing methods of haploid breeding and plant tissue culture methods to derive progeny of the CN1703-derived sunflower plant.

VI. TISSUE CULTURES AND IN VITRO REGENERATION OF SUNFLOWER PLANTS

As is well known in this art, tissue culture of sunflower may be used for the in vitro regeneration of a sunflower plant, note, for example Finer J., Direct somatic embryogenesis and plant regeneration from immature embryos of hybrid sunflower (*Helianthus annuus* L.) on a high sucrose-containing medium, Plant Cell Reports (1987) 6: 372-374, the disclosure of which is incorporated by reference in its entirety. Accordingly, a further aspect of the invention relates to tissue cultures of the inbred sunflower plant designated CN1703, to tissue cultures of hybrid and derived sunflower plants obtained from CN1703, to plants obtained from such tissue cultures and to the use of tissue culture methodology in plant breeding. The term "tissue culture" includes a composition comprising isolated cells of the same type, isolated cells of a different type, or a collection of such cells organized into parts of a plant. Exemplary tissue cultures are protoplasts, calli and plant cells that are intact in plants or parts of plants, such as embryos, pollen, flowers, kernels, leaves, stalks, roots, root tips, anthers, stigmas, and the like. In a preferred embodiment, the tissue culture comprises embryos, protoplasts, meristematic cells, pollen, leaves or anthers derived from immature tissues of these plant parts.

A. Immature Embryo Culture

To obtain immature embryos for callus culture initiation, seeds are harvested from a sunflower plant, e.g., an inbred sunflower plant CN1703, a hybrid sunflower plant having CN1703 as a parent or a CN1703-derived sunflower plant, they are germinated in the greenhouse and pollinations are performed daily for 1 week following flowering. Immature embryos are utilized as explants from 7 to 14 days post-pollination. Intact immature seeds are surface sterilized by placement in a 20% commercial bleach solution containing 0.05% Tween-20.

After 20 minutes, the seeds are rinsed 4 times with sterile, distilled water. Immature zygotic embryos are excised from the seeds. Tissue culture media typically, contain amino acids, salts, sugars, hormones, and vitamins. Most of the media employed to regenerate inbred and hybrid plants have some similar components; the media differ in the composition and proportions of their ingredients depending on the particular application envisioned. An exemplary media culture on which the excised immature zygotic embryos can be placed contains MS salts, B-5 vitamins with 12% sucrose, 3.3 mg/L dicamba and 1 mg/L 2,4-D. Following initiation of somatic embryogenesis, resulting somatic embryos are placed onto a hormone-free medium containing MS Salts, B-5 vitamins, and 2% sucrose for embryo development and germination. Modifications of these and other basic media may facilitate growth of recipient cells at specific developmental stages.

Plantlets derived from somatic embryos are transferred to vermiculite and watered with ¼ strength MS salts. Plantlets are initially covered and gradually exposed to ambient humidity over a 2 week period. One having ordinary skill in the art would understand that explants from other tissues such as immature anther tissue, intercalary meristems and leaf bases, apical meristems, and immature stigmas may also be the subject of callus culture initiation.

Primary regenerants ($R_1$ plants) are self- or sib-pollinated after an additional time in pots, and $R_1$ seed is collected post-pollination. Alternately, when self- or sib-pollinations are not possible, plants may be outcrossed to elite inbreds.

B. Additional Tissue Cultures and Regeneration

Other means for preparing and maintaining plant tissue cultures are well known in the art. By way of example, other regeneration media have been used to produce regenerated plants (U.S. Pat. Nos. 4,681,849 and 4,687,743); regeneration of sunflowers via embryogenesis and organogenesis has been described (U.S. Pat. Nos. 4,670,391, 4,670,392 and 4,673, 648; and, Alibert, G. et al., Sunflower tissue and cell cultures and their use in biotechnology, Plant Physiol. Biochem., 1994, 32 (1), 31-44) and a tissue culture comprising organs such as cotyledons have been used to produce regenerated plants (U.S. Patent Publication No. 2002/0157138). The disclosure of the aforementioned patents and publications is specifically incorporated herein by reference.

VII. MALE STERILITY

While hand emasculation and hand pollination may be used to make crosses and obtain hybrid sunflower seed for growing an F1 generation in the breeding nursery, such methodologies are too laborious and expensive to use for commercial production of hybrid sunflower seed.

Other methods for controlling male fertility in sunflower plants offer the opportunity for improved plant breeding, particularly for the development of sunflower hybrids which require the implementation of a male sterility system to prevent the inbred parent plants from self-pollination.

Accordingly, another aspect of the present invention is male-sterile inbred sunflower plants, typically designated CN1703A and the production of hybrid sunflower seed using a male sterility system with such an inbred female parent plants that are male sterile. In the event that inbred sunflower line CN1703 is employed as the female parent, CN1703 can be rendered male-sterile by, for example, introduction of a male-sterile cytoplasm into the B-line by a backcross procedure.

Plants of cytoplasmic male-sterile (CMS) inbreds are male sterile as a result of factors resulting from cytoplasmic as opposed to the nuclear genome. Thus, this characteristic is inherited exclusively through the female parent in sunflower plants since CMS plants are fertilized with pollen from another inbred that is not male-sterile. Pollen from the second inbred may or may not contribute genes that make the hybrid plants male-fertile. A-lines may be crossed with fertility-restorer, R-lines to produce hybrid seed. Conventional backcrossing methodology may be used to introgress the CMS trait into inbred CN1703. The cytoplasmic male sterile A-line is maintained by pollination from the male-fertile counterpart B-line. The increased A-line seed is male-sterile because the fertile cytoplasmic factor from the B-line is not transmitted by pollen.

R-lines (males) are homozygous for a dominant cytoplasmic male sterility fertility restoration allele and possess either a fertile or a sterile cytoplasmic factor. Like B-lines, R-lines also produce viable pollen. Hybrid seed is produced by pollinating A-line plants with pollen from R-line plants. The resulting hybrid seeds are heterozygous at the nuclear locus for the dominant fertility restoration allele and possess the sterile cytoplasmic factor. Thus, the hybrid seed will grow into plants which produce viable pollen.

Chemically induced male sterility may also be used in the production of hybrid sunflower seed. Chemicals that induce male sterility include gametocides, pollen suppressants, and chemical hybridizing agents. The general procedure is to use a foliar spray before flowering, which inhibits production of viable pollen, but does not injure the reproductive organs or affect seed development. If the treatment is successful and all of the pollen killed, self-pollination will not occur in the treated plants, but the flowers will set seed freely from cross-pollination. In such a case, the parent plants used as the male may either not be treated with the chemical agent or may include a genetic factor which causes resistance to the sterilizing effects of the chemical agent.

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described by Patterson in U.S. Pat. Nos. 3,861,709 and 3,710,511. These and all patents referred to are incorporated by reference. In addition to these methods, U.S. Pat. No. 5,432,068, discloses a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene which confers male fertility to be transcribed.

Other methods of conferring genetic male sterility exist in the art. These methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et. al, EP089/3010153.8 publication no 329, 308 and PCT application PCT/CA90/00037 published as WO 90/08828).

The presence of a male-fertility restorer gene results in the production of a fully fertile $F_1$ hybrid progeny. If no restorer gene is present in the male parent, male-sterile hybrids are obtained. Such hybrids are useful where the vegetative tissue of the sunflower plant is used, e.g., for silage, but in most cases, the seeds will be deemed the most valuable portion of the crop, so fertility of the hybrids in these crops must be restored. Therefore, one aspect of the present invention concerns crossing inbred sunflower plant CN1703 with an inbred sunflower plant comprising a single gene capable of restoring male fertility in an otherwise male-sterile inbred or hybrid plant. Examples of male-sterility genes and corresponding restorers which could be employed within the inbred of the invention are well known to those of skill in the art of plant breeding and are disclosed in, for example, U.S. Pat. Nos. 5,530,191, 5,689,041, 5,741,684, and 5,684,242, the disclosures of which are each specifically incorporated herein by reference in their entirety.

VIII. SUNFLOWER TRANSFORMATION

With the advent of molecular biological techniques that have allowed the isolation and characterization of genes that encode specific protein products, scientists in the field of plant biology developed a strong interest in engineering the genome of plants to contain and to express foreign genes, or additional, or modified versions of native or endogenous genes (perhaps driven by different promoters) to alter the traits of a plant in a specific manner. Such foreign, additional and/or modified genes are referred to herein collectively as "transgenes." The present invention, in particular embodiments, also relates to transformed versions of the claimed inbred sunflower line CN1703 containing one or more transgenes.

Plant transformation involves the construction of an expression vector which will function in plant cells. Such a vector comprises DNA comprising a gene under control of or operatively linked to a regulatory element. The expression vector may contain one or more such operably linked gene/ regulatory element combinations. The vector(s) may be in the form of a plasmid, and can be used, alone or in combination with other plasmids, to provide transformed sunflower plants, using transformation methods as described below to incorporate transgenes into the genetic material of the sunflower plant(s).

A. Expression Vectors for Sunflower Transformation/Marker Genes

Expression vectors include at least one genetic marker, operably linked to a regulatory element that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase H (nptII) gene, isolated from a bacterial source, which when placed under the control of plant regulatory signals confers resistance to kanamycin. Fraley et al., *Proc. Natl. Acad. Sci. U.S.A.* 80: 4803 (1983). Another commonly used selectable marker gene is the hygromycin phosphotransferase gene which confers resistance to the antibiotic hygromycin. Vanden Elzen et al., *Plant Mol. Biol.* 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.* 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or bromoxynil. Comai et al., *Nature* 317: 741-744 (1985), Gordon-Kamm et al., *Plant Cell* 2: 603-618 (1990) and Stalker et al., *Science* 242: 419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987), Teeri et al., *EMBO J.* 8: 343 (1989), Koncz et al., *Proc. Natl. Acad. Sci. U.S.A.* 84: 131 (1987), De Block et al., *EMBO J.* 3: 1681 (1984). Another approach to the identification of a relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, IMAGENE GREEN™, p. 1-4 (1983) and Naleway et al., *J. Cell Biol.* 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

B. Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter is a promoter which is under environmental control or is induced in response to chemical or hormonal stimuli. Examples of environmental conditions that may effect transcription by inducible promoters include anaerobic conditions or the presence of light. Examples of chemicals that induce expression including salicyclic acid and ABA. Tissue-specific, tissue-preferred, cell type specific, and inducible promoters constitute the class of "non-constitutive" promoters. A "constitutive" promoter is a promoter which is active under most environmental conditions and in all cells.

1. Inducible Promoters

An inducible promoter is operably linked to a gene for expression in sunflower. Optionally, the inducible promoter is operably linked to a nucleotide sequence encoding a signal sequence which is operably linked to a gene for expression in sunflower. With an inducible promoter the rate of transcription increases in response to an inducing agent. Any inducible promoter can be used in the instant invention. See Ward et al. Plant Mol. Biol.22: 361-366 (1993). Exemplary inducible promoters include, but are not limited to, that from the ACEI system which responds to copper (Mett et al. PNAS 90: 4567-4571 (1993)); In2 gene from sunflower which responds to benzenesulfonamide herbicide safeners (Hershey et al., Mol. Gen. Genetics 227: 229-237 (1991) and Gatz et al., Mol. Gen. Genetics 243: 32-38 (1994)) or Tet repressor from Tn20 (Gatz et al., Mol. Gen. Genet. 227: 229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88: 0421 (1991).

2. Constitutive Promoters

A constitutive promoter is operably linked to a gene for expression in sunflower or the constitutive promoter is operably linked to a nucleotide sequence encoding a signal sequence which is operably linked to a gene for expression in sunflower. Many different constitutive promoters can be used in the present invention. Exemplary constitutive promoters include, but are not limited to, the promoters from plant viruses such as the 35S promoter from CaMV (Odell et al., Nature 313: 810-812 (1985) and the promoters from such genes as rice actin, maize ubiquitin, and corn H3 histone. Also, the ALS promoter, a XbaI/NcoI fragment 5' to the *Brassica napus* ALS3 structural gene (or a nucleotide sequence that has substantial sequence similarlity to the XbaI/NcoI fragment) represents a particularly useful constitutive promoter. See PCT application WO96/30530.

3. Tissue-Specific or Tissue-Preferred Promoters

A tissue-specific promoter is operably linked to a gene for expression in sunflower. Optionally, the tissue-specific promoter is operably linked to a nucleotide sequence encoding a signal sequence which is operably linked to a gene for expression in sunflower. Plants transformed with a gene of interest operably linked to a tissue-specific promoter produce the protein product of the transgene exclusively, or preferentially, in a specific tissue. Any tissue-specific or tissue-preferred promoter can be utilized in the instant invention. Exemplary tissue-specific or tissue-preferred promoters include, but are not limited to, a seed-preferred promoter such as that from the phaseolin gene; a leaf-specific and light-induced promoter such as that from cab or rubisco; an anther-specific promoter such as that from LAT52; a pollen specific promoter such as that from Zm13 or a microspore-preferred promoter such as that from apg.

C. Signal Sequences For Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Any signal sequence known in the art is contemplated by the present invention.

D. Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods.

According to a preferred embodiment, the transgenic plant provided for commercial production of foreign protein is sunflower. In another preferred embodiment, the biomass of interest is seed. For the relatively small number of transgenic plants that show higher levels of expression, a genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to:

1. Genes that Confer Resistance to Pests or Disease and that Encode:

(a) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (Arabidopsis RSP2 gene for resistance to *Pseudomonas syringae*).

(b) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998.

(c) A lectin. See, for example, the disclosure by Van Damme et al., Plant Molec. Biol. 24: 25 (1994), who disclose the nucleotide sequences of several *Clivia miniata* mannose-binding lectin genes.

(d) A vitamin-binding protein such as avidin. See PCT application US93/06487 the contents of which are hereby incorporated by reference. The application teaches the use of avidin and avidin homologues as larvicides against insect pests.

(e) An enzyme inhibitor, for example, a protease inhibitor or an amylase inhibitor. See, for example, Abe et al., J. Biol. Chem. 262: 16793 (1987) (nucleotide sequence of rice cysteine proteinase inhibitor), Huub et al., Plant Molec. Biol. 21: 985 (1993) (nucleotide sequence of cDNA encoding tobacco proteinase inhibitor I), and Sumitani et al., Biosci. Biotech. Biochem. 57: 1243 (1993) (nucleotide sequence of *Streptomyces nitrosporeus* α-amylase inhibitor).

(f) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(g) An insect-specific peptide or neuropeptide which, upon expression, disrupts the physiology of the affected pest. For example, see the disclosures of Regan, J. Biol. Chem. 269: 9 (1994) (expression cloning yields DNA coding for insect diuretic hormone receptor), and Pratt et al., Biochem. Biophys. Res. Comm. 163: 1243 (1989) (an allostatin is identified in *Diploptera puntata*). See also U.S. Pat. No. 5,266,317 to Tomalski et al., who disclose genes encoding insect-specific, paralytic neurotoxins.

(h) An insect-specific venom produced in nature by a snake, a wasp, etc. For example, see Pang et al., Gene 116: 165 (1992), for disclosure of heterologous expression in plants of a gene coding for a scorpion insectotoxic peptide.

(i) An enzyme responsible for an hyperaccumulation of a monterpene, a sesquiterpene, a steroid, hydroxamic acid, a phenylpropanoid derivative or another non-protein molecule with insecticidal activity.

(j) An enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi-4-2 polyubiquitin gene.

(k) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a corn calmodulin cDNA clone.

(1) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(m) A membrane permease, a channel former or a channel blocker. For example, see the disclosure by Jaynes et al., Plant Sci. 89: 43 (1993), of heterologous expression of a cecropin-β lytic peptide analog to render transgenic tobacco plants resistant to *Pseudomonas solanacearum*.

(n) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(p) A virus-specific antibody. See, for example, Tavladoraki et al, Nature 366: 469 (1993), who show that transgenic plants expressing recombinant antibody genes are protected from virus attack.

(q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonate. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(r) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

2. Genes that Confer Resistance to a Herbicide, for Example:

(a) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241 (1988), and Mild et al., Theor. Appl. Genet. 80: 449 (1990), respectively.

(b) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., Bio/Technology 7: 61 (1989), describe the production of transgenic plants that express chimeric bar genes coding for phospinothricin acetyl transferase activity. Exemplary of genes conferring resistance to phenoxy proprionic acids and cyclohexones, such as sethoxydim and haloxyfop, are the Acc1-S1, Acc1-S2 and Acc1-S3 genes described by Marshall et al., Theor. Appl. Genet. 83: 435 (1992).

(c) A herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

3. Genes that Confer or Contribute to a Value-Added Trait, Such as:

(a) Modified fatty acid metabolism, for example, by transforming a plant with an antisense gene of stearoyl-ACP desaturase to increase stearic acid content of the plant. See Knultzon et al., Proc. Natl. Acad. Sci. USA 89: 2624 (1992).

(b) Decreased phytate content:

(i) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene.

(ii) A gene could be introduced that reduces phytate content.

(iii) Modified carbohydrate composition effected, for example, by transforming plants with a gene coding for an enzyme that alters the branching pattern of starch. See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtillus* levansucrase gene), Pen et al., Bio/Technology 10: 292 (1992) (production of transgenic plants that express *Bacillus lichenifonnis* α-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley α-amylase gene), and Fisher et al., Plant Physiol. 102: 1045 (1993) (corn endosperm starch branching enzyme II).

E. Methods for Sunflower Transformation

Numerous methods for plant transformation have been developed, including biological and physical, plant transformation protocols. See, for example, Mild et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, inc., Boca Raton, 1993) pages 89-119.

1. *Agrobacterium*-mediated Transformation

One method for introducing an expression vector into plants is based on the natural transformation system of *Agrobacterium*. See, for example, Horsch et al., Science 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant. Sci.10:1 (1991). Descriptions of *Agrobacterium* vector systems and methods for *Agrobacterium*-mediated gene transfer are provided by Gruber et al., supra, Mild et al., supra, and Moloney et al., Plant Cell Reports 8: 238 (1989). See also, U.S. Pat. No. 5,591,616, issued Jan. 7, 1997. The first sunflower transformations with engineered strains of *Agrobacterium* were reported in 1983 in which Phaseolin was inserted into T-DNA of the Ti plasmid and inoculated to sunflower seedlings. Murai et al. (1983) "Phaseolin Gene From Bran is Expressed After Transfer to Sunflower", Science, 222:475482. Sunflower is susceptible to *Agrobacterium* infection and it remains the most efficient and popular transformation protocol. Knittel et al., "Transformation of Sunflower/*Helianthus annuus* L.) A Retrievable Protocol", Plant Cell Rep. 14: 81-86; Malone-Schoneberg, J., et al. 1994, "Stable Transformation of Sunflower Using *Agrobacterium* and Split Embryonic Axis Explants", Plant Science, 103: 119-207.

2. Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., The Plant Journal 6: 271-282 (1994); U.S. Pat. No. 5,591,616, issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm (See e.g., U.S. Pat. No. 5,550,318; U.S. Pat. No. 5,736,369, U.S. Pat. No. 5,538,880; and PCT Publication WO 95/06128). The expression vector is introduced into plant tissues with a biolistic device that accelerates the microprojectiles to speeds of 300 to 600 m/s which is sufficient to penetrate plant cell walls and membranes. Sanford et al, Part. Sci. Technol. 5: 27 (1987), Sanford, J. C., Trends Biotech. 6: 299 (1988), Klein et al., Bio/Technology 6: 559-563 (1988), Sanford, J. C., Physiol Plant 79: 206 (1990), Klein et al., Biotechnology 10: 268 (1992). In sunflower, several target tissues can be bombarded with DNA-coated microprojectiles in order to produce transgenic plants, including, for example, callus (Type I or Type II), immature embryos, and meristematic tissue. In sunflower microprojectile bombardment efficiency is low. Experiments with sunflower meristems designed to compare stable transformation efficiency of microprojectile bombardment to deliver plasmid DNA with bombardment used only to induce wounds to facilitate *Agrobacterium* transformation showed the frequency of positive transformants nearly 300 fold higher in the latter protocol. Bidney et al., "Microprojectile Bombardment of Plant Tissues Increases Transformation Frequency by *Agrobacterium tumefaciens*", Plant Mol. Biol. 18: 301-313 (1993).

Another method for physical delivery of DNA to plants is sonication of target cells. Zhang et al., Bio/Technology 9: 996 (1991). Alternatively, liposome or spheroplast fusion have been used to introduce expression vectors into plants. Deshayes et al., EMBO J., 4: 2731 (1985), Christou et al., Proc Natl. Acad. Sci. U.S.A. 84: 3962 (1987). Direct uptake of DNA into protoplasts using $CaCl_2$ precipitation, polyvinyl alcohol or poly-L-ornithine have also been reported. Hain et al., Mol. Gen. Genet.199: 161 (1985) and Draper et al., Plant Cell Physiol. 23: 451 (1982). Electroporation of protoplasts and whole cells and tissues have also been described. U.S. Pat. No. 5,384,253 and Donn et al. In Abstracts of VIIth International Congress on Plant Cell and Tissue Culture IAPTC, A2-38, p 53 (1990); D'Halluin et al., Plant Cell 4: 1495-1505 (1992) and Spencer et al., Plant Mol. Biol. 24: 51-61 (1994).

Other methods which have been described for the genetic transformation include, electrotransformation (U.S. Pat. No. 5,371,003) and silicon carbide fiber-mediated transformation (U.S. Pat. No. 5,302,532 and U.S. Pat. No. 5,464,765).

Following transformation of sunflower target tissues, expression of the above-described selectable marker genes allows for preferential selection of transformed cells, tissues and/or plants, using regeneration and selection methods now well known in the art. Several sunflower transformant protocols have evolved which allow for the identification of transformants without the need for selectable markers. Nutler et al. 1987, "Factors Affecting the Level of Kanamycin Resistance in Transformed Sunflower Cells", Plant Physiol. 84: 1185-1192. See also, Bidney, D., et al., supra, using intact meristem explants and analyzing gene in leaf tissue via protein methods such as ELISA or enzyme assay or nucleic acid methods such as PCR or RT-PCTR.

The foregoing methods for transformation would typically be used for producing transgenic inbred lines. Transgenic inbred lines could then be crossed, with another (non-transformed or transformed) inbred line, in order to produce a transgenic hybrid sunflower plant. Alternatively, a genetic trait which has been engineered into a particular sunflower line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid sunflower plant containing a foreign gene in its genome into a line or lines which do not contain that gene.

IX. GENETIC COMPLEMENTS

In addition to phenotypic observations, a sunflower plant can also be described by its genotype. The genotype of a sunflower plant can be described through a genetic marker profile which can identify plants of the same variety, a related variety or be used to determine or to validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs), Isozyme Electrophoresis and Isoelectric Focusing. For example, see Gedil, M. A. 1999. Marker development, genome mapping, and cloning of candidate diseasese resistance genes in sunflower, *Helianthus annuus* L. Ph.D. Thesis, Oregon State Univ., Corvallis; Yu, J.-K., Mangor, J., Thompson, L., Edwards, K. J., Slabaugh, M. B., and Knapp, S. J. 2002. Allelic diversity of simple sequence repeat markers among elite inbred lines in cultivated sunflower. Genome (in press); and, Tang, S., Yu, J.-K., Slabaugh, M. B., Shintani, D. K., and Knapp, S. J. 2002. Simple sequence repeat map of the sunflower genome. Theor. Appl. Genetics (in press), which are incorporated by reference herein in its entirety.

Particular markers used for these purposes are not limited to the set of markers disclosed herewithin, but are envisioned to include any type of genetically stable marker and marker profile which provides a means of distinguishing varieties. In addition to being used for identification of inbred parents, a hybrid produced through the use of CN1703 or its parents, and identification or verification of the pedigree of progeny plants produced through the use of CN1703, the genetic marker profile is also useful in breeding and developing backcross conversions.

Means of performing genetic marker profiles using SSR polymorphisms are well known in the art. SSRs are genetic markers based on polymorphisms in repeated nucleotide sequences, such as microsatellites. The phrase "simple sequence repeats" or "SSR" refers to di-, tri- or tetra-nucleotide repeats within a genome. The repeat region may vary in length between genotypes while the DNA flanking the repeat is conserved such that the primers will work in a plurality of genotypes. A polymorphism between two genotypes represents repeats of different lengths between the two flanking conserved DNA sequences. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR). The PCR® detection is done by the use of two oligonucleotide primers flanking the polymorphic segment of repetitive DNA followed by DNA amplification. This step involves repeated cycles of heat denaturation of the DNA followed by annealing of the primers to their complementary sequences at low temperatures, and extension of the annealed primers with DNA polymerase. Size separation of DNA fragments on agarose or polyacrylamide gels following amplification, comprises the major part of the methodology.

DNA isolation and amplification were performed in the present invention as follows. DNA was extracted from plant leaf tissue using DNeasy 96 Plant Kit from Qiagen, Inc. (Valencia, Calif., U.S.A.) following an optimized September 2002 manufacturer's protocol. PCR amplifications were performed using a Qiagen HOTSTAR™ Taq master mix in an 8 μl reaction format as follows: 2 μl DNA (5 ng/μL+6 μL of master mix). The PCR conditions were as follows: 12 mins. at 95° C., 40 cycles of 5 seconds at 94° C., 15 seconds at 55° C., 30 seconds at 72° C., 30 mins. at 72° C., followed by cooling to 4° C. Following isolation and amplification, markers can be scored by gel electrophoresis of the amplification products. Scoring of marker genotype is based on the size of the amplified fragment as measured by molecular weight (MW) rounded to the nearest integer. Multiple samples, comprised of fluorescently labeled DNA fragments were processed in an ABI 3700 capillary-based machine and precise allele sizing and locus genotyping were done by running GeneScan and Genotyper software (PE Applied Biosystems, Foster City, Calif.). When comparing lines, it is preferable if all SSR profiles are performed in the same lab. An SSR service is available to the public on a contractual basis by Paragen, Research Triangle Park, N.C. (formerly Celera AgGen of Davis, Calif.). Primers used for the SSRs suggested herein are publicly available from Oregon State University, College of Agricultural Sciences, Crops & Soil Science program. The chromosome locations on which such markers are located and the location on such chromosome are generally reported in the Database. SSR information is provided in TABLE 3.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Method for prediction of hybrid performance from genetic marker data are disclosed in U.S. Pat. No. 5,492,547, the disclosure of which is specifically incorporated herein by reference in its entirety. Such predictions may be made using any suitable laboratory-based techniques for the analysis, comparison and characterization of plant genotype.

The most widely used of these laboratory techniques are Isozyme Electrophoresis and RFLPs. Isozyme Electrophoresis is a useful tool in determining genetic composition, although it has relatively low number of available markers and the low number of allelic variants among sunflower inbreds. RFLPs have the advantage of revealing an exceptionally high degree of allelic variation in sunflower and the number of available markers is almost limitless. The present invention provides a genetic complement of the inbred sunflower plant variety designated CN1703. Further provided by the invention is a hybrid genetic complement, wherein the complement is formed by the combination of a haploid genetic complement from CN1703 and another haploid genetic complement. Means for determining such a genetic complement are well-known in the art.

As used herein, the phrase "genetic complement" means an aggregate of nucleotide sequences, the expression of which defines the phenotype of a sunflower plant or a cell or a tissue of that plant. By way of example, a sunflower plant is genotyped to determine a representative sample of the inherited markers it possesses. Markers are alleles at a single locus. They are preferably inherited in codominant fashion so that the presence of both alleles at a diploid locus is readily detectable and they are free of environmental variation, i.e., their heritability is 1. This genotyping is preferably performed on at least one generation of the descendant plant for which the numerical value of the quantitative trait(s) of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus.

The SSR genetic marker profile of inbred CN1703 was determined. Because an inbred is essentially homozygous at all relevant loci, an inbred should, in almost all cases, have both the alleles of one size at each locus. In contrast, a diploid genetic marker profile of a hybrid should be the sum of those parents, e.g., if one inbred parent had the allele 168 (base pairs) at a particular locus, and the other inbred parent had 172, the hybrid is 168,172 by inference. Subsequent generations of progeny produced by selection and breeding are expected to be of genotype 168, 172, or 168,172 for that locus by inference. When the $F_1$ plant is used to produce an inbred, the locus should be either 168 or 172 for that position. Surprisingly, it has been observed that in certain instances, novel SSR genotypes arise during the breeding process. For example, a genotype of 170 may be observed at a particular locus positions from the cross of parental inbreds with 168 and 172 at that locus. Such a novel SSR genotype may further define an inbred plant from the parental inbreds from which it was derived. An SSR genetic marker profile of CN1703 is presented in Table 3 wherein representative measured fragment lengths of alleles are given.

TABLE 3

| Public Name Of Marker | CN1703 Measured Fragment Length |
| --- | --- |
| HA1062 | 318.46 |
| HA1420 | 235.23 |
| HA0904 | 263.3 |
| HA0966 | 145.15 |
| HA1297 | 200.55 |
| HA1526 | 273.01 |
| HA1575 | 254.76 |
| HA0851 | 296.25 |
| HA0808 | 162.27 |
| HA0688 | 118.23 |
| HA0908 | 175.5 |
| HA0837 | 227.77 |
| HA0827 | 321.76 |
| HA1348 | 242.14 |
| HA1726 | 187.97 |
| HA0804 | 220.52 |
| HA1339 | 192.27 |
| HA1350 | 110.72 |
| HA1549 | 248.74 |

TABLE 3-continued

| Public Name Of Marker | CN1703 Measured Fragment Length |
| --- | --- |
| HA0813 | 345.33 |
| HA0705 | 240.51 |
| HA0976 | 248.51 |
| HA0919 | 312.18 |
| HA1546 | 281.78 |
| HA0695 | 188.36 |
| HA0686 | 134.25 |
| HA0796 | 135.93 |
| HA1017 | 158.72 |
| HA1703 | 266.16 |
| HA1090 | 343.08 |
| HA1363 | 261.46 |
| HA1360 | 315.26 |
| HA0861 | 151.14 |
| HA1449 | 258.63 |

The present invention also provides a hybrid genetic complement formed by the combination of a haploid genetic complement of the sunflower plant CN1703 with a haploid genetic complement of a second sunflower plant. Means for combining a haploid genetic complement from the foregoing inbred with another haploid genetic complement may comprise any method for producing a hybrid plant from CN1703. It is contemplated that such a hybrid genetic complement can be prepared using in vitro regeneration of a tissue culture of a hybrid plant of this invention.

In addition, plants and plant parts substantially benefiting from the use of CN1703 in their development such as CN1703 comprising a backcross conversion, or transgene, may be identified by having a molecular marker profile with a high percent identity to CN1703. Such a percent identity might be 85%, 90%, 91%, 92%, 93%, 94%, 95%, 96%, 97%, 98%, 99%, 99.5% or 99.9% identical to CN1703.

The SSR profile of CN1703 also can be used to identify derived varieties and other progeny lines developed from the use of CN1703, as well as cells and other plant parts thereof. Progeny plants and plant parts produced using CN1703 may be identified by having a molecular marker profile of at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from sunflower plant CN1703.

All publications, patents and patent applications mentioned in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in some detail by way of illustration and example for purposes of clarity and understanding. However, it should be appreciated by those having ordinary skill in the art that certain changes and modifications such as single gene modifications and mutations, somoclonal variants, variant individuals selected from large populations of the plants of the instant inbred and the like may be practiced within the scope of the invention, as limited only by the scope of the appended claims, without departing from the true concept, spirit, and scope of the invention.

What is claimed is:

1. A seed of sunflower inbred line designated CN1703, or a part thereof, a representative sample of the seed having been deposited under ATCC Accession No. PTA-6885.

2. The seed or a part thereof of claim 1, wherein the part is selected from the group consisting of pericarp, germ and endosperm.

3. The seed of claim 1, further comprising a coating.

4. A substantially homogenous composition of the sunflower seed of claim 1.

5. A method for producing inbred sunflower seed, comprising:
 (a) planting seed of claim 1 in proximity to itself;
 (b) growing plants from the seed under self-pollinating conditions; and,
 (c) harvesting resultant seed.

6. An inbred sunflower seed produced by the method of claim 5.

7. The method of claim 5, further comprising pre-treating the seed of step (a) before performing step (a).

8. The method of claim 5, further comprising treating the growing plants or soil surrounding the growing plants with an agricultural chemical.

9. A sunflower plant produced by growing the seed of claim 1.

10. A part of the sunflower plant of claim 9, selected from the group consisting of an intact plant cell, a plant protoplast, an embryo, a pollen, a stigma, a flower, a head, a seed, a hull, a leaf, a stalk, a root, a root tip, an anther, a cortex, a pith, an involuntary bract, a ray flower, a disk flower, a pappi, a nectary, an interfloral bract, a trichome, a filament, a calyx and a stem.

11. Pollen of the plant of claim 9.

12. An ovule of the plant of claim 9.

13. A sunflower plant, or a part thereof, having all the physiological and morphological characteristics of the sunflower plant of claim 9, wherein the plant part is selected from the group consisting of an intact plant cell, a plant protoplast, an embryo, an ovule, a pollen, a stigma, a flower head, a seed, a hull, a leaf, a root, a root tip, an anther, a cortex, a pith, an involucral bract, a ray flower, a disk flower, a pappi, a stalk, a nectary, an interfloral bact, a trichome, a filament, a calyx and a stem.

14. A substantially homogenous population of sunflower plants of claim 9.

15. The substantially homogenous population of sunflower plants of claim 14, wherein the population is present in a field and the field further comprises other, different sunflower plants.

16. A method for producing an inbred sunflower plant, comprising:
 (a) crossing inbred sunflower plant CN1703, a representative sample of seed of the plant having been deposited under ATCC Accession No. PTA-6885, with another different sunflower plant to yield a F1 progeny sunflower plant;
 (b) harvesting seed from the F1 progeny sunflower plant;
 (c) growing the F1 progeny sunflower seed from step (b) under self-pollinating or sib-pollinating conditions for about 5 to about 7 generations to produce inbred sunflower plants;
 (d) selecting the plants of step (c) for a desirable trait.

17. A method of introducing a desired trait into sunflower inbred line CN1703 comprising:
 (a) crossing CN1703 plants grown from CN1703 seed, a representative sample of the CN1703 seed having been deposited under ATCC Accession No. PTA-6885, with plants of another sunflower line that comprise a desired trait to produce F1 progeny plants;
 (b) selecting F1 progeny plants that have the desired trait;
 (c) crossing selected progeny plants with CN1703 plants to produce backcross progeny plants;
 (d) selecting for backcross progeny plants that comprise the desired trait and physiological and morphological characteristics of sunflower inbred line CN1703; and
 (e) performing steps (c) and (d) one or more times in succession to produce the selected or higher backcross progeny plants that comprise the desired trait and all of the physiological and morphological characteristics of sunflower inbred line CN1703 listed in Table 1 as determined at the 5% significance level when grown in the same environmental conditions.

18. The method of claim 16, wherein the plants of the other sunflower line comprise a desired trait selected from the group consisting of male sterility, herbicide resistance, insect resistance, and resistance to bacterial, fungal and viral disease.

19. The method of claim 16, further comprising using genetic markers to compare a genetic complement of a progeny plant with a genetic complement of the CN1703 plant.

20. The method of claim 16, further comprising using direct or indirect selection to determine whether the desired trait is present in a progeny plant.

21. A method for producing a sunflower plant, comprising:
 a) crossing the inbred sunflower plant of claim 9 with another different sunflower plant to produce a diploid progeny plant;
 b) generating a haploid progeny plant from the diploid progeny plant;
 c) generating a diploid plant from the haploid progeny plant; and,
 d) selecting the diploid sunflower plant.

22. The method of claim 21, wherein the haploid progeny plant is generated by culturing a haploid explant from the diploid progeny plant.

23. The method of claim 21, wherein the haploid progeny plant is generated by crossing the progeny plant with another, different plant that induces haploid sunflower plants.

24. The method of claim 23, wherein the other, different plant is a sunflower plant that comprises a haploid-inducing gene.

25. The method of claim 21, the diploid plant of step c) is generated by subjecting the haploid progeny plant to a treatment which induces chromosome doubling in the cultured explant.

26. The method of claim 21, wherein the diploid plant of step c) is generated by self pollinating the haploid progeny plant.

27. A method for producing a mutated sunflower plant, comprising:
 a) inducing a mutation in the sunflower plant, or a part thereof, of claim 9; and,
 b) selecting mutated sunflower plants.

28. The method of claim 27, wherein the mutation is artificially induced by a method selected from the group consisting of elevated temperature, long-term seed storage, tissue culture conditions, radiation, and chemical mutagenesis.

29. A method for producing an inbred sunflower plant, comprising:
 a) growing first generation hybrid sunflower plants having a parent sunflower plant grown from CN1703 seed, a representative sample of the seed having been deposited under ATCC Accession No. PTA-6885;
 b) inbreeding the first generation hybrid sunflower plants or crossing the first generation hybrid sunflower plants with different sunflower plants to yield progeny sunflower seed;

c) growing the progeny sunflower seed of step b) to yield further progeny sunflower seed;

d) repeating the inbreeding or the crossing and the growing steps of b) and c) from about 1 to about 7 times to generate inbred sunflower plants.

30. A method for producing a hybrid sunflower seed comprising crossing a first inbred parent sunflower plant with a second inbred parent sunflower plant and harvesting resultant hybrid sunflower seed, wherein the first inbred sunflower plant is the sunflower plant of claim 9.

31. The method according to claim 30, wherein the first inbred sunflower plant is male-sterile.

32. A method for producing a hybrid sunflower seed comprising the steps of:
(a) planting in pollinating proximity seeds of a first and a second inbred parent sunflower plants, wherein the first inbred sunflower plant is the sunflower plant of claim 9;
(b) cultivating the seeds of the first and the second inbred sunflower plants into plants that bear flowers;
(c) controlling the male fertility of the first or the second inbred sunflower plant to produce a male sterile sunflower plant;
(d) allowing cross-pollination to occur between the first and second inbred sunflower plants; and,
(e) harvesting seeds produced on the male sterile sunflower plant.

33. The method according to claim 32, wherein the first inbred sunflower plant is a female parent and is cytoplasmic male sterile.

34. A hybrid sunflower seed produced by the method of claim 31.

35. A hybrid sunflower plant, or a part thereof, produced by growing the hybrid sunflower seed of claim 34, wherein the plant part is selected from the group consisting of an intact plant cell, a plant protoplast, an embryo, an ovule, a pollen, a stigma, a flower head, a seed, a hull, a leaf, a root, a root tip, an anther, a cortex, a pith, an involucral bract, a ray flower, a disk flower, a pappi, a stalk, a nectary, an interfloral bact, a trichome, a filament, a calyx and a stem.

36. An F1 hybrid seed produced by crossing the inbred sunflower plant according to claim 9 with another, different sunflower plant.

37. A hybrid sunflower plant, or a part thereof, produced by growing the hybrid sunflower seed of claim 36, wherein the plant part is selected from the group consisting of an intact plant cell, a plant protoplast, an embryo, an ovule, a pollen, a stigma, a flower head, a seed, a hull, a leaf, a root, a root tip, an anther, a cortex, a pith, an involucral bract, a ray flower, a disk flower, a pappi, a stalk, a nectary, an interfloral bact, a trichome, a filament, a calyx and a stem.

38. A method for producing a CN1703-derived sunflower plant, comprising:
a) crossing inbred sunflower line CN1703, representative seed of the line having been deposited under ATCC Accession No. PTA-6885, with a second sunflower plant to yield progeny sunflower seed; and
b) growing said progeny sunflower seed, under plant growth conditions, to yield said CN1703-derived sunflower plant.

39. A CN1703-derived sunflower plant, or a part thereof, produced by the method of claim 38.

40. The method of claim 38, further comprising:
c) crossing the CN1703-derived sunflower plant with itself or another sunflower plant to yield additional CN1703-derived progeny sunflower seed;

d) growing the progeny sunflower seed of step c) under plant growth conditions, to yield additional CN1703-derived sunflower plants; and
e) repeating the crossing and growing steps of c) and d) from 0 to 7 times to generate further CN1703-derived sunflower plants.

41. The method of claim 38, still further comprising utilizing plant tissue culture methods and/or haploid breeding to derive progeny of said CN1703-derived sunflower plant.

42. A tissue culture of regenerable cells from the sunflower plant of claim 9.

43. A tissue culture according to claim 42, the cells or protoplasts of the tissue culture being from a tissue selected from the group consisting of an intact plant cell, a plant protoplast, an embryo, a pollen, a stigma, a flower, a head, a seed, a hull, a plant DNA, a leaf, a stalk, a root, a root tip, an anther, a cortex, a pith, an involuntary bract, a ray flower, a disk flower, a pappi, a nectary, an interfloral bract, a trichome, a filament, a calyx and a stem.

44. A sunflower plant regenerated from the tissue culture of claim 42, wherein the regenerated plant expresses all the morphological and physiological characteristics of inbred line CN1703, a representative sample of the seed of inbred line CN1703 having been deposited under ATCC Accession No. PTA-6885.

45. A tissue culture of regenerable cells from the hybrid sunflower plant of claim 35.

46. A method for regenerating a sunflower plant comprising the steps of:
(a) culturing an explant comprising a tissue selected from the group consisting of a tissue obtained from inbred sunflower plant CN1703, a representative sample of seed of the plant having been deposited under ATCC Accession No. PTA-6885, an immature tissue obtained from a hybrid sunflower plant having CN1703 as a parent, and a CN1703-derived sunflower plant; and,
(b) initiating regeneration.

47. The process of claim 46, wherein the explant is an immature tissue.

48. A method for producing a male sterile CN1703 sunflower plant, comprising:
(a) crossing the inbred sunflower plant of claim 9, with a cytoplasmic male sterile sunflower plant which generates haploids;
(b) identifying haploid plants; and,
(c) crossing the haploid plants with the inbred sunflower plant CN1703, a representative sample of CN1703 seed having been deposited under ATCC Accession No. PTA-6885, to produce male sterile CN1703 sunflower plants.

49. A sunflower plant, or a part thereof, produced by transforming a plant according to claim 9 with one or more transgenes, wherein the genetic material of the transformed plant or parts thereof contains one or more transgenes operably linked to one or more regulatory elements, and, wherein the plant part is selected from the group consisting of an intact plant cell, a plant protoplast, an embryo, an ovule, a pollen, a stigma, a flower head, a seed, a hull, a leaf, a root, a root tip, an anther, a cortex, a pith, an involucral bract, a ray flower, a disk flower, a pappi, a stalk, a nectary, an interfloral bact, a trichome, a filament, a calyx and a stem.

50. A method for producing a sunflower plant that contains in its genetic material one or more transgenes, comprising crossing the sunflower plant of claim 49 with either a second plant of another sunflower line, or a non-transformed sunflower plant of the line CN1703, a representative sample of the CN1703 seed having been deposited under ATCC Accession No. PTA-6885, so that the genetic material of the progeny that result from the cross contains the transgene(s) operably linked to a regulatory element.

51. A sunflower plant according to claim 49, wherein said one or more transgenes comprises a gene conferring upon the sunflower plant tolerance to a herbicide.

52. A sunflower plant according to claim 51, wherein the herbicide is glyphosate, gluphosinate, a sulfonylurea or an imidazolinone herbicide, a hydroxyphenylpyruvate dioxygenase inhibitor or a protoporphyrinogen oxidase inhibitor.

53. A sunflower plant according to claim 49, wherein the one or more transgenes comprises a gene conferring upon the sunflower plant insect resistance, disease resistance or virus resistance.

54. A sunflower plant according to claim 53, wherein the gene conferring upon the sunflower plant insect resistance is a *Bacillus thuringiensis* gene.

55. A seed of the plant according to claim 49.

56. A sunflower plant, or a part thereof, produced by the method of claim 49, wherein the plant part is selected from the group consisting of an intact plant cell, a plant protoplast, an embryo, an ovule, a pollen, a stigma, a flower head, a seed, a hull, a leaf, a root, a root tip, an anther, a cortex, a pith, an involucral bract, a ray flower, a disk flower, a pappi, a stalk, a nectary, an interfloral bact, a trichome, a filament, a calyx and a stem.

57. A method for developing a sunflower plant in a sunflower plant breeding program, comprising:

a) utilizing the inbred sunflower plant CN1703, a representative sample of seed having been deposited under ATCC Accession No. PTA-6885 [genetic marker dataset in Table 3].

58. The method of claim 57, wherein the step (a) comprises comparing the inbred sunflower plant genetic marker dataset in Table 3 to a hybrid sunflower plant genetic marker dataset to determine a relationship between the datasets.

59. A method for producing a population of CN1703 progeny inbred sunflower plants comprising:

(a) obtaining a first generation progeny sunflower seed comprising the plant of claim 9 as a parent;

(b) growing the first generation progeny sunflower seed to produce F1 generation sunflower plants and obtaining self or sib pollinated seed from the F1 generation sunflower plants; and, (c) producing successive filial generations to obtain a population of CN1703 progeny inbred sunflower plants.

60. The population of CN1703 progeny inbred sunflower plants produced by the method of claim 59, the population, on average, deriving 50% of its alleles from CN1703, a representative sample of seed of the plant having been deposited under ATCC Accession No. PTA-6885.

61. A cytoplasmic male sterile sunflower plant produced according to the method of claim 48.

* * * * *